(12) United States Patent
Korman (10) Patent No.: US 9,101,308 B2
(45) Date of Patent: Aug. 11, 2015

(54) SIMPLE SUGAR CONCENTRATION SENSOR AND METHOD

(71) Applicant: K Sciences GP, LLC, San Antonio, TX (US)

(72) Inventor: Valentin Korman, Huntsville, AL (US)

(73) Assignee: K SCIENCES GP, LLC, San Antonio, TX (US)

(*) Notice: Subject to any disclaimer, the term of this patent is extended or adjusted under 35 U.S.C. 154(b) by 0 days.

(21) Appl. No.: 14/293,356

(22) Filed: Jun. 2, 2014

(65) Prior Publication Data

US 2014/0268103 A1    Sep. 18, 2014

Related U.S. Application Data

(63) Continuation of application No. 13/950,054, filed on Jul. 24, 2013, now Pat. No. 8,743,355.

(60) Provisional application No. 61/714,731, filed on Oct. 16, 2012.

(51) Int. Cl.
| | | |
|---|---|---|
| *G01N 33/48* | (2006.01) | |
| *A61B 5/145* | (2006.01) | |
| *G01N 21/21* | (2006.01) | |
| *A61B 5/1455* | (2006.01) | |

(52) U.S. Cl.
    CPC ........... *A61B 5/14532* (2013.01); *A61B 5/1455* (2013.01); *G01N 21/21* (2013.01)

(58) Field of Classification Search
    USPC .......................................................... 356/39
    See application file for complete search history.

(56) References Cited

U.S. PATENT DOCUMENTS

| 3,724,957 | A | | 4/1973 | Tamate et al. |
|---|---|---|---|---|
| 4,014,321 | A | | 3/1977 | March |
| 4,699,514 | A | | 10/1987 | Schmidt et al. |
| 4,901,728 | A | * | 2/1990 | Hutchison .................... 600/316 |
| 5,009,230 | A | * | 4/1991 | Hutchinson .................. 600/316 |

(Continued)

FOREIGN PATENT DOCUMENTS

| DE | 102009020701 A1 | 11/2010 |
|---|---|---|
| JP | 2005265592 A | 9/2005 |

(Continued)

OTHER PUBLICATIONS

International Search Report mailed Nov. 22, 2013 in corresponding PCT application PCT/US13/65228, 2 pages.

(Continued)

*Primary Examiner* — Roy M. Punnoose
(74) *Attorney, Agent, or Firm* — Gardere Wynne Sewell LLP (57) ABSTRACT

A glucose sensor comprising an optical energy source having an emitter with an emission pattern; a first polarizer intersecting the emission pattern; a second polarizer spaced a distance from the first polarizer and intersecting the emission pattern, the second polarizer rotated relative to the first polarizer by a first rotational amount Θ; a first optical detector intersecting the emission pattern; a second optical detector positioned proximal to the second polarizer, the first polarizer and the second polarizer being positioned between the optical energy source and the second optical detector, the second optical detector intersecting the emission pattern; a compensating circuit coupled to the second optical detector; and a subtractor circuit coupled to the compensating circuit and the first optical detector.

25 Claims, 9 Drawing Sheets

(56) References Cited

U.S. PATENT DOCUMENTS

| | | | |
|---|---|---|---|
| 5,383,452 A * | 1/1995 | Buchert | 600/347 |
| 5,477,327 A * | 12/1995 | Bergman | 356/367 |
| 5,896,198 A | 4/1999 | Chou et al. | |
| 6,016,435 A | 1/2000 | Maruo et al. | |
| 6,370,407 B1 | 4/2002 | Kroeger et al. | |
| 6,567,678 B1 | 5/2003 | Oosta et al. | |
| 6,615,061 B1 | 9/2003 | Khalil et al. | |
| 6,708,048 B1 | 3/2004 | Chance | |
| 6,775,564 B1 | 8/2004 | Peters et al. | |
| 7,245,952 B2 | 7/2007 | Cameron | |
| 7,248,905 B2 | 7/2007 | Fukuda et al. | |
| 7,299,079 B2 | 11/2007 | Rebec et al. | |
| 7,801,581 B2 | 9/2010 | Diab | |
| 8,180,422 B2 | 5/2012 | Rebec | |
| 8,452,360 B2 | 5/2013 | Mandelis et al. | |

FOREIGN PATENT DOCUMENTS

| | | | |
|---|---|---|---|
| WO | WO-0060350 A2 | 10/2000 | |
| WO | WO-0122871 A1 | 4/2001 | |

OTHER PUBLICATIONS

Written Opinion mailed Nov. 22, 2013 in corresponding PCT Application No. PCT/US2013/065228; 6 pages.

* cited by examiner

SIMPLE SUGAR CONCENTRATION SENSOR AND METHOD

CROSS-REFERENCES TO RELATED APPLICATIONS

This application is a continuation of U.S. patent application Ser. No. 13/950,054 filed Jul. 24, 2013, which claims the benefit of U.S. Provisional Patent Application No. 61/714,731, filed Oct. 16, 2012; both of said priority applications are incorporated by reference herein in their entirety.

STATEMENT REGARDING FEDERALLY-SPONSORED RESEARCH OR DEVELOPMENT

Not applicable.

BACKGROUND OF THE INVENTION

1. Field of the Invention

The present invention relates to monitoring of simple sugar (or monosaccharide) content within a fluid. More specifically, the invention uses an optical energy source in combination with polarizers to determine the change in a sugar level (e.g., glucose) of a subject fluid relative to a baseline concentration, such as blood.

2. Description of the Related Art

Simple sugar changes the polarization of the optical energy passing through it according to the equation $\Theta = \alpha \times L \times C$, where L is the travel length of the energy through the fluid in which the sugar is concentrated, C is the sugar concentration, and a is a constant that depends on the type of sugar, wavelength of the energy, and the fluid. If L and a are known, by measuring the change in polarization of energy passing through a sugar-containing fluid relative to a baseline measurement, the sugar concentration of the fluid can be derived.

This principal may be used, for example, to non-invasively determine the glucose concentration of human blood. Normal blood has a non-zero glucose concentration C, which causes a change in polarization for energy passing through the blood. For a glucose concentration of 70 mg/dL and an $\alpha=45.62$ ($\times 10^{-6}$) degrees/mm/(mg/dL), energy of wavelength 633 nm and a 3.0 mm path length will have a rotation $\Theta$ of 0.00958 degrees. Measuring the change in rotation caused by the sugar allows derivation of the current sugar concentration.

SUMMARY OF THE INVENTION

The present invention may be used to monitor sugar (e.g., glucose) in a fluid, and provides numerous advantages over traditional techniques that rely on a standard polarization analyzer, which requires actively moving parts and angular resolution precision to 0.01 degrees. First, the present invention is non-invasive, which lowers the risk of contamination. Second, the present invention may provide an ability to stream real-time, continuous data. Third, the present invention provides a low operating cost.

The invention includes an optical energy source having an emitter with an emission pattern; a first polarizer intersecting the emission pattern; a second polarizer spaced a distance from the first polarizer and intersecting the emission pattern, the second polarizer rotated relative to the first polarizer by a first rotational amount $\Theta$; a first optical detector intersecting the emission pattern; a second optical detector positioned proximal to the second polarizer, the first polarizer and the second polarizer being positioned between the optical energy source and the second optical detector, the second optical detector intersecting the emission pattern; a compensating circuit coupled to the second optical detector; and a subtractor circuit coupled to the compensating circuit and the first optical detector.

DESCRIPTION OF THE VARIOUS EMBODIMENTS

Figure 1:
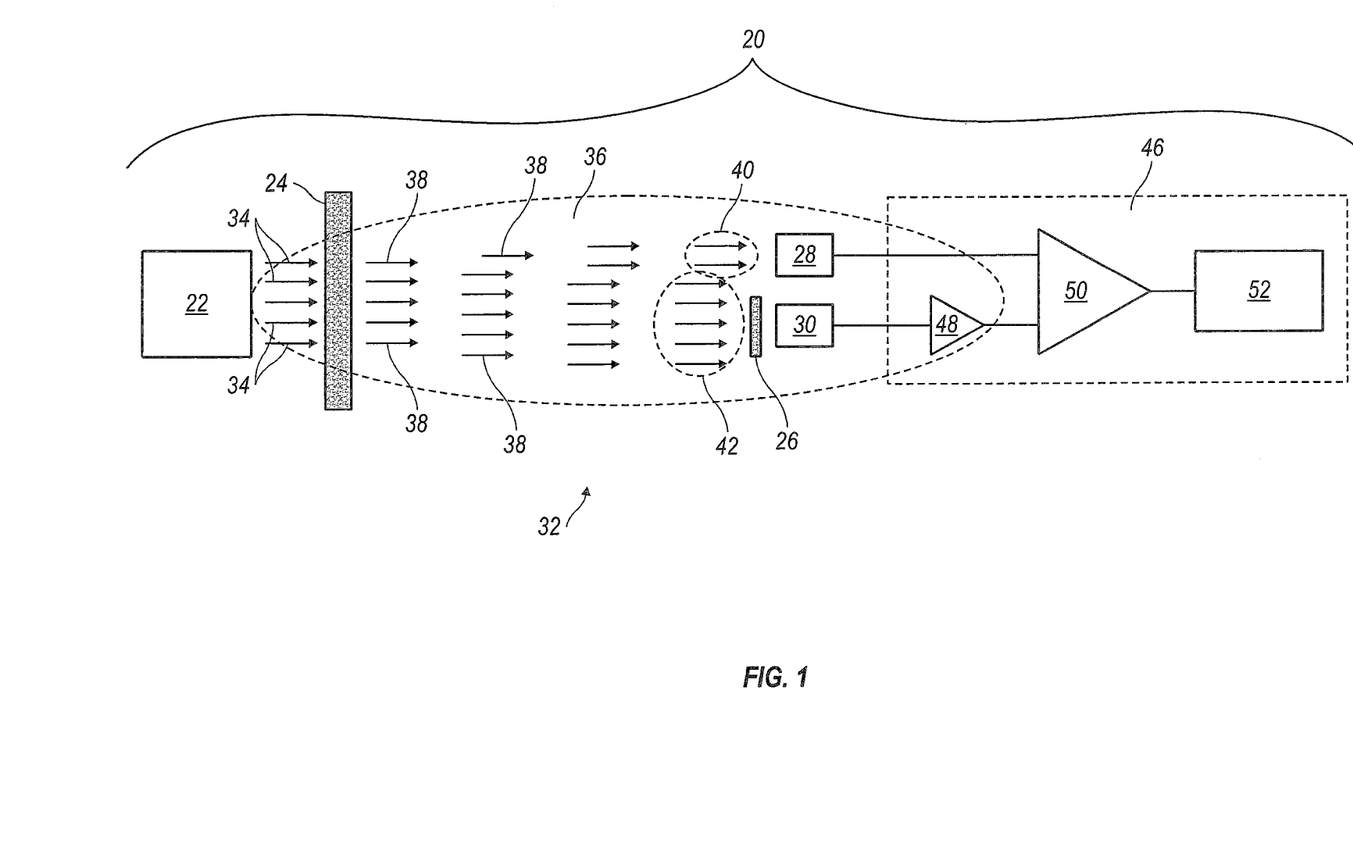
FIG. 1 is a system diagram of an embodiment of the invention.

FIG. 1 shows one embodiment 20 of the invention, which comprises an optical energy source 22, a first polarizer 24, a second polarizer 26 spaced a distance from the first polarizer 24 having a rotation $\Theta$ relative to the first polarizer 24, a first optical energy detector 28, a second optical energy detector 30 collocated with the first detector 28, and a circuit 46. Each of the first and second optical detectors 28, 30 are oriented to receive optical energy passing through a space 32. In the preferred embodiment, the detectors 28, 30 are silicon detectors. As used herein, "collocated" means being positioned adjacent each other so that, all else being equal, light from a common source will enter each of the detectors with approximately equal intensity. In addition, although the embodiment discloses the use of silicon detectors, other types of detectors may be used (e.g., photoresistors).

When actuated, the energy source 22 produces initial optical energy 34 having an emission pattern 36. The energy source 22 is preferably a red light source, such as a red light-emitting diode (LED) or a laser, but may alternatively be near-infrared. Ultimately, the initial optical energy 34 must be of a wavelength that may be affected by the presence of sugar in the subject fluid while also passing through the other vessel in which the fluid is contained.

The first polarizer 24 is positioned proximal to the source 22, such that the initial optical energy 34 passes through the first polarizer 24 and becomes polarized energy 38. The polarized energy 38 traverses the space 32 between the first and second polarizer 24, 26, where a first portion 40 of the polarized energy 38 is detected by a first optical detector 28 and a second portion 42 of the polarized energy 38 passes through a second polarizer 26 to the second optical energy detector 30. Notably, first detector and second detector 28, 30 are collocated, despite the proximity of second polarizer 26 to the second detector 30. Because the space 32 is empty in FIG. 1, the polarized energy 38 passing through the space 32 is not rotated by, for example, the presence of a sugar in a fluid.

Preferably, the first and second polarizers 24, 26 are a linearly-polarized film because such film is inexpensive compared to other available alternatives. Such film, however, is optimal for energy wavelengths in the visible spectrum. Other polarizers may be used, provided that the selected wavelength of the energy source 22 is chosen to optimally correspond. For example, an alternative polarizer may be wire-grid or holographic, which is optimally configured for use in the present invention with energy of near-infrared and infrared wavelengths.

Preferably, the difference in rotation between the polarizers 24, 26 is forty-five degrees (or an integral multiple of forty-five degrees) plus the rotation caused by the baseline. In this optimal case, a change in concentration relative to the baseline at least initially moves along the most linear portion of a sine wave, which makes detecting the change in rotation easier compared to moving further away from where the slope of the wave is 1 and further towards where the slope is 0 (i.e., the crest and troughs of the sine wave). For example, when used with a baseline glucose concentration 100 mg/dL over a length of L, Θ equals 0.014 degrees. In this case, the rotation between the polarizers should be 45.014 degrees. The greater the change in concentration from the baseline, however, the more non-linear the correlation of the rotation to the change in concentration.

The first and second detectors 28, 30 are electrically coupled to the circuit 46. The circuit 46 has a compensating circuit 48, a subtractor circuit 50, and a gain circuit 52. The first detector 28 is directly coupled to the subtractor circuit 50. The second detector 30 is coupled to the compensating circuit 48, which boosts the gain of the signal produced by the second detector 30 by an amount sufficient to compensate for the loss of intensity attributable to the portion 42 of polarized energy 38 passing through the polarized film and the effects of polarization due to the baseline concentrations in the fluid, but the compensating circuit 48 does not compensate for the loss in intensity resulting from changes in polarization due to the concentration change from some baseline itself. The subtractor circuit 50 produces a signal that is the difference between the signals received from the first and second detectors 28, 30. The gain circuit 52 amplifies the signal to a usable level.

Notably, in alternative embodiments, the compensating circuit 48 may be an attenuator coupled to the first detector 28 to equalize the intensity of the received optical energy, with the objective being that the difference in energy seen by the first detector 28 and the second detector 30 relates to the rotation of the energy rather than its amplitude. Similarly, the subtractor circuit 50 may be replaced by a Wheatstone or similar bridge.

Figure 2:
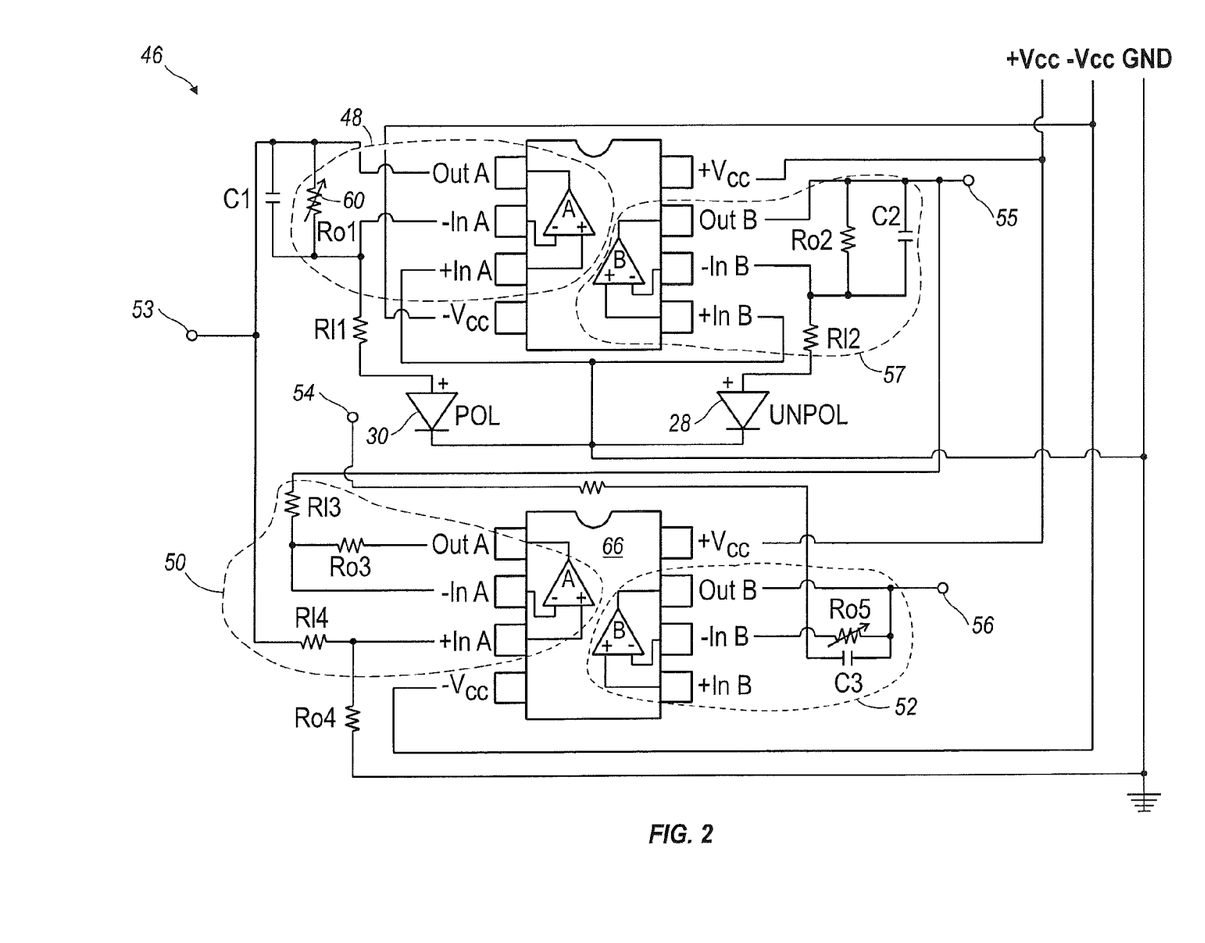
FIG. 2 is a circuit diagram of the circuit described with reference to FIG. 1.

Referring to FIG. 2, the outputs of the first and second detectors 28, 30 are provided to the circuit 46. The circuit 46 comprises the compensating circuit 48 having a potentiometer Ro1, the subtractor circuit 50, first and second 30-Hz low pass filters that included Ro1 and C1, and Ro2 and C2, and the gain circuit 52. The subtractor circuit 50 and the gain circuit 52 incorporate an OPA 211KP operational amplifier IC 66. The low pass filters reject any noise at the detectors 28, 30. Polarized output 53 and the unpolarized outputs 55 are fed to the subtractor circuit 50, which comprises Ro3, Ro4, Rl3 and Rl4. The subtractor circuit output 54 is then provided to the gain circuit 52 comprising Ro5 and C3. The final signal is provided at the gain circuit output 56. The embodiment includes an optional unity gain circuit 57 for phase-matching purposes.

Figure 3:
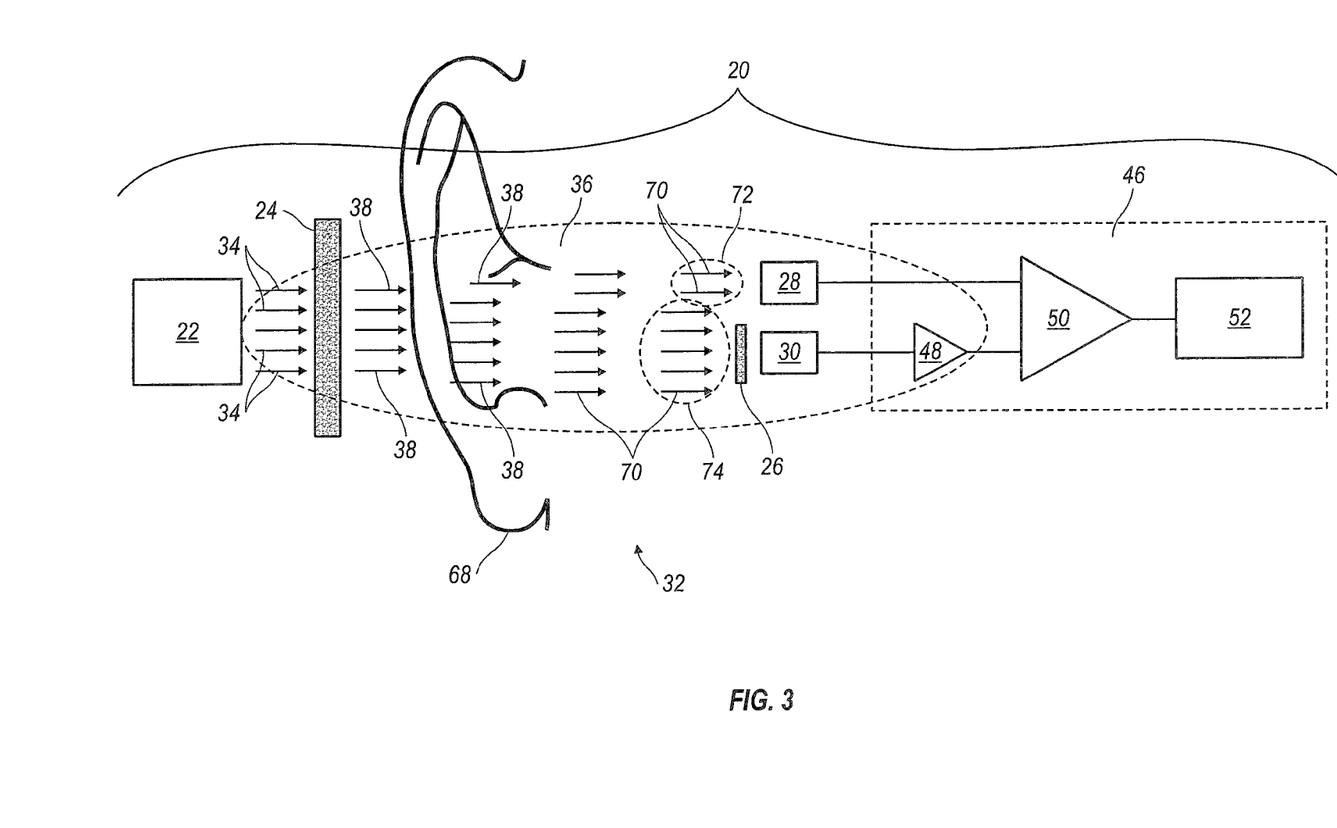
FIG. 3 is the system diagram of FIG. 1 showing the embodiment in use with a human ear.

FIG. 3 shows the embodiment 20 in use with a human ear 68, at least a portion of which occupies the space 32. The preferred orientation of the ear 68 within the space 32 is so that the polarized energy 38 passes through the ear 68 generally parallel to a lateral axis, where L is the distance along the axis of the measured fluid. For most human ears, L is approximately three millimeters of capillary-rich and blood vessel-rich skin.

When actuated, the energy source 22 produces initial optical energy 34 having the emission pattern 36. The initial energy 34 passes through the first polarizer 24, and is of a wavelength to which the non-sugar components of the ear 68 (i.e., skin, blood, tissue, cartilage) are, to at least some extent, transparent.

After passing through the first polarizer 24, the initial energy 34 becomes polarized energy 38. Glucose within the blood in the ear 68, however, will cause a change in polarization of the energy 38 according to $\Theta = \alpha \times L \times C$, causing the rotated energy 70 exiting the ear to have a first rotation $\Theta_1$.

The intensity of a first portion 72 of the rotated energy 70 is detected by the first detector 28. The intensity of a second portion 74 of the rotated energy 70 passes through the second polarizer 26 and is detected by the second detector 30. Each of the first and second detectors 28, 30 produces a signal representative of the received intensity. Because the intensity of the rotated energy 70 received by the second detector 30 is only the intensity of the rotated energy component passing through the second polarizer 26, by measuring the difference in intensities at the detectors 28, 30, the rotation caused by the glucose in the ear 70 can be derived, from which the changed in glucose concentration relative to a baseline can be determined.

To determine the baseline, prior to use, the embodiment 20 is calibrated to a baseline glucose concentration of seventy mg/dL (a "normal" concentration for human blood) by changing the potentiometer 60 to compensate for the difference in intensities of energy received by the first and second detectors 28, 30. Thus, any change in measured rotation represents a change in glucose concentration from some baseline (e.g., 70 mg/dL).

An alternative embodiment of the invention is calibrated to a baseline glucose concentration of 100 mg/dL using wavelength of 650 nm, resulting in a rotation of 45.028 degrees of the second polarizer relative to the first polarizer. This results range of resulting rotation of the baseline plus or minus 0.2 degrees for a glucose concentration of between 30 mg/dL and 300 mg/dL. Thus, a glucose concentration of 30 mg/dL will result in a rotational difference between the detectors of 0.0096 degrees, whereas a glucose concentration of 300 mg/dL will result in a rotational difference of 0.0273 degrees in the opposite direction of the direction of the 30 mg/dL concentration.

There are at least two methods for calibrating the invention. First and preferably, during fabrication of each sensor, a sample control serum or a similar component that would rotate the polarization state a known amount would be inserted in the space. This control would provide a simulated known glucose concentration for use in adjusting the device to the proper calibrated settings. Alternatively, the user/wearer can take an initial reading with the sensor and additionally take a near-simultaneous reading with another glucose sensor (e.g., a blood stick meter). This value from the other sensor would be input into the sensor with user input means such as a knobs, buttons and the like connected to a microcontroller.

Figure 4A:
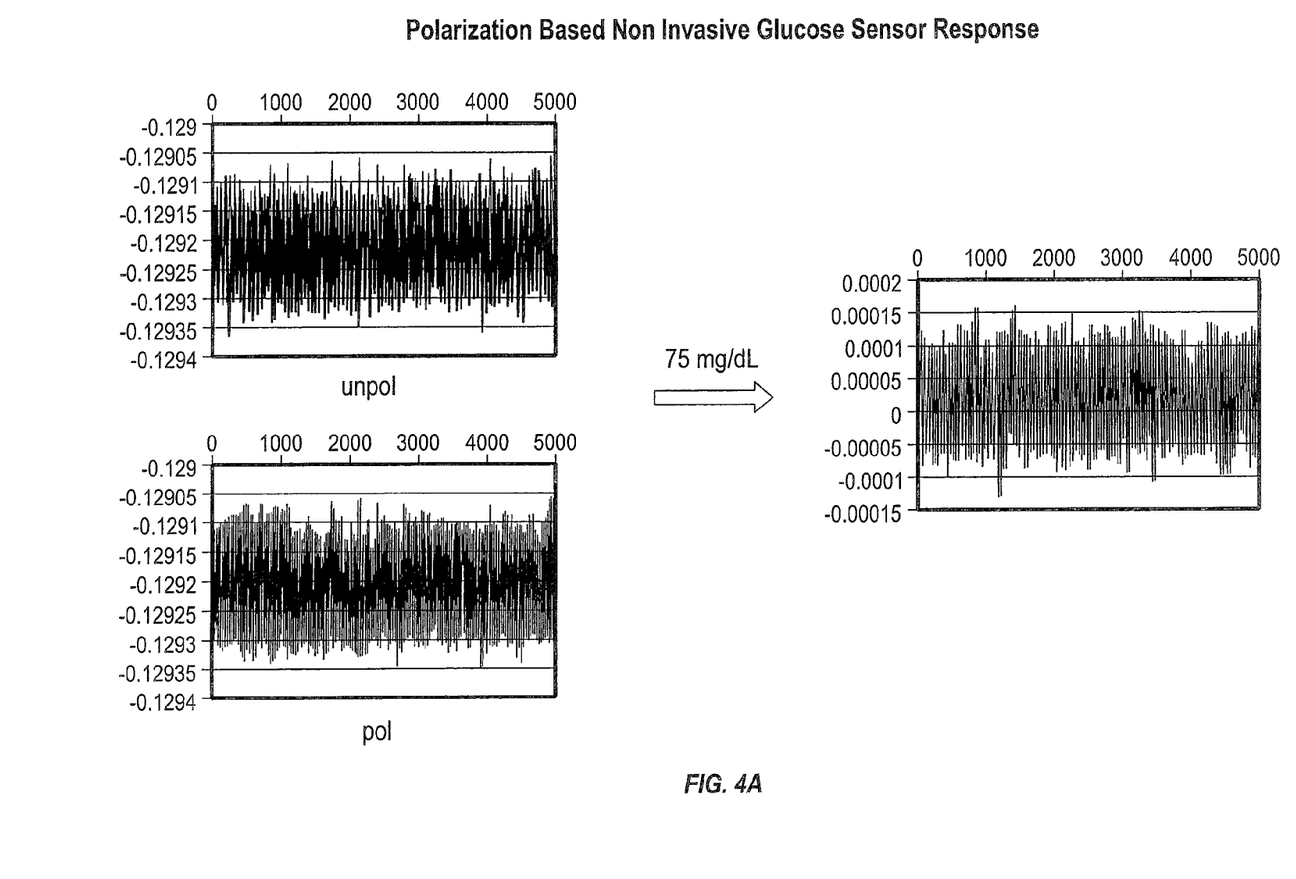
FIG. 4A-4C show actual data from an embodiment of the present invention used to derive sugar concentrations for three separate cases.
Figure 4B:
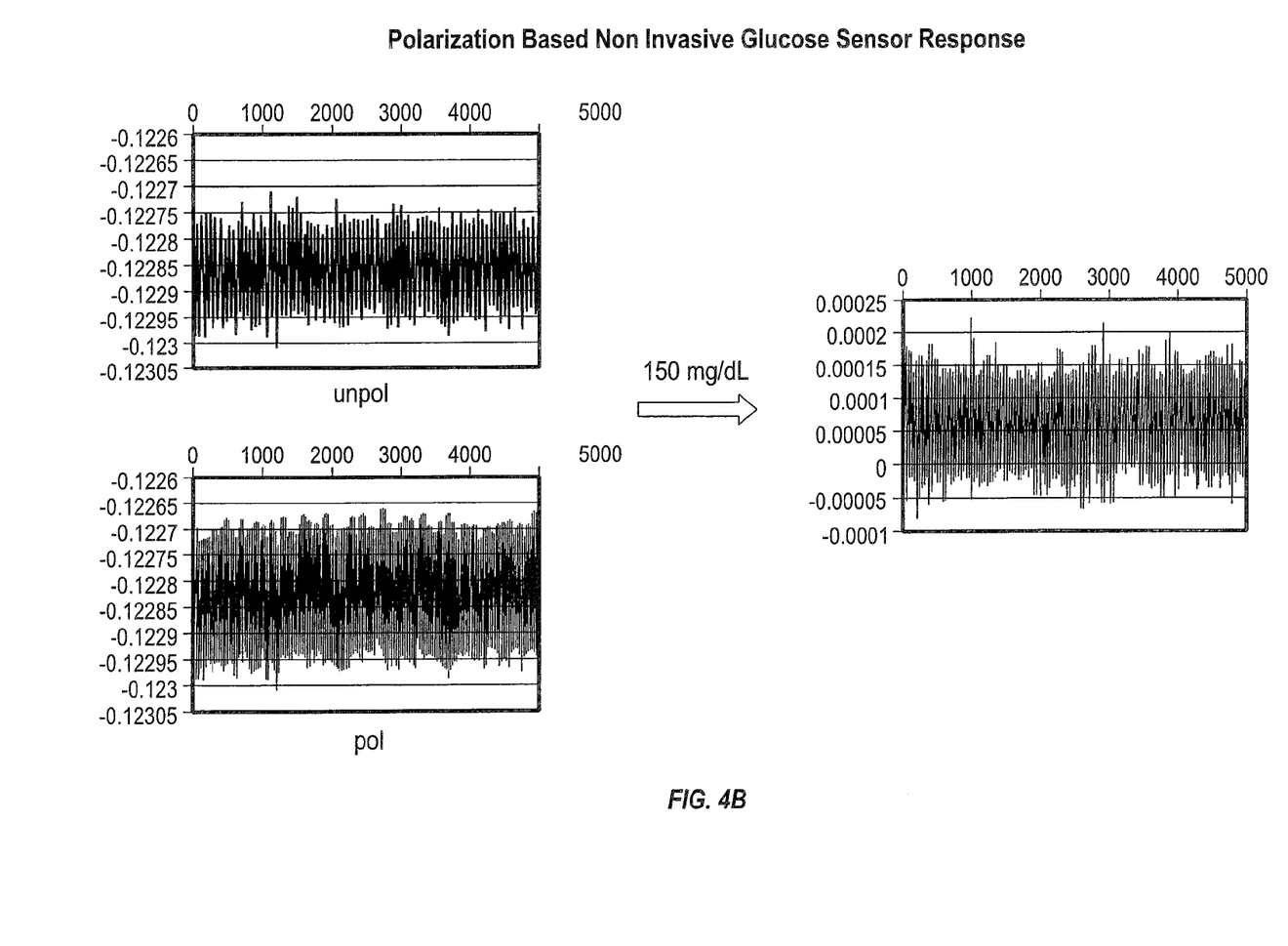
Figure 4C:
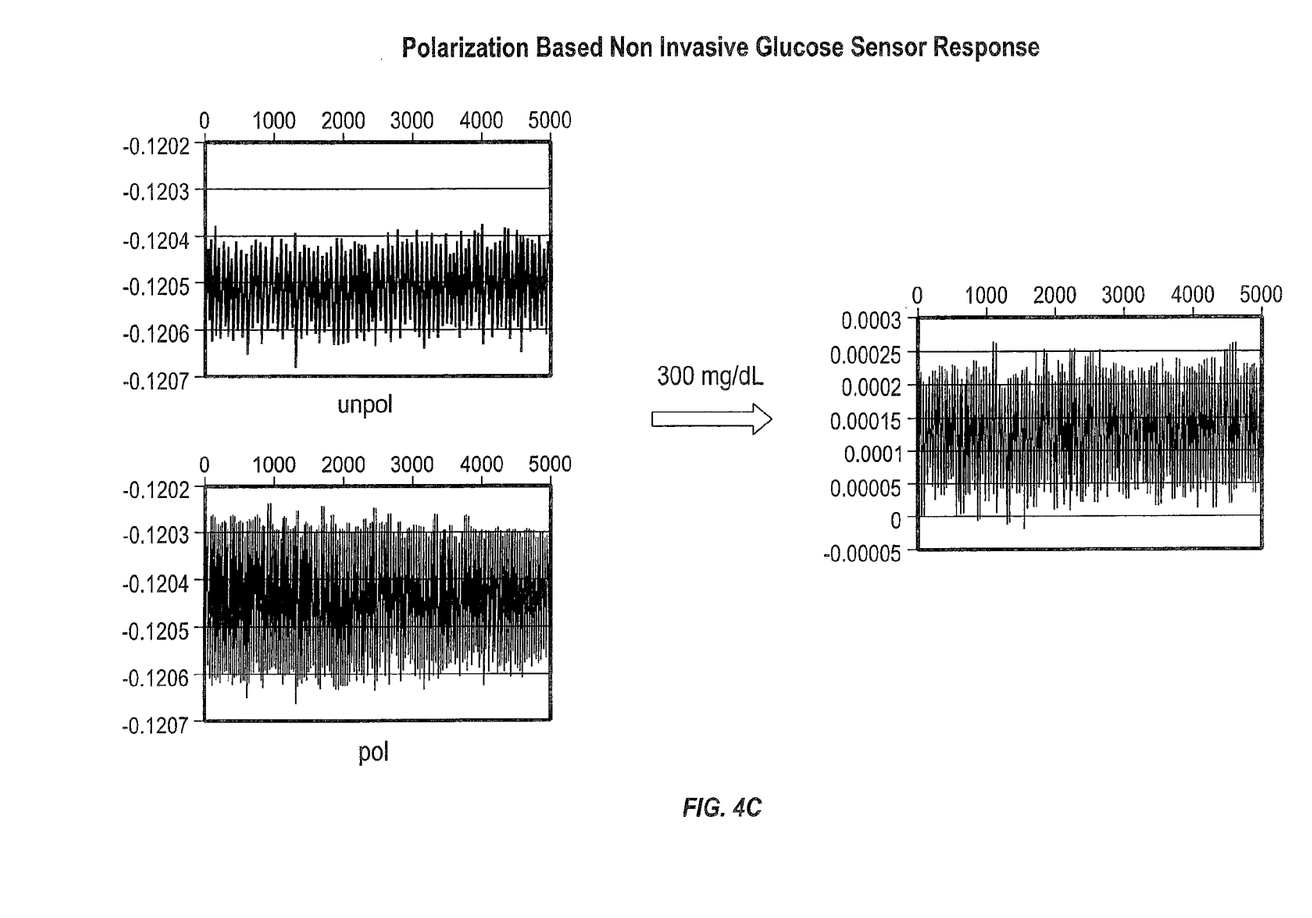

FIGS. 4A-4C shows actual data from an embodiment of the invention used to detect glucose concentrations of 75 mg/dL, 150 mg/dL, and 300 mg/DL. The left side of each example shows actual signals received from the polarized detector 28 and the non-polarized detector 30. The right side of each example shows the output of the subtractor circuit. The embodiment is calibrated for a baseline of 75 mg/dL. In FIG. 4A, the subtractor circuit averages to zero, indicating no change from the baseline. In FIG. 4B, the subtractor circuit averages to approximately 0.00005 Volts. In FIG. 4C, the output of the subtractor circuit averages to approximately 0.0001 Volts, or twice the middle example, which is expected give that the concentration of the bottom example is twice the concentration of shown in FIG. 4B.

Figure 5A:
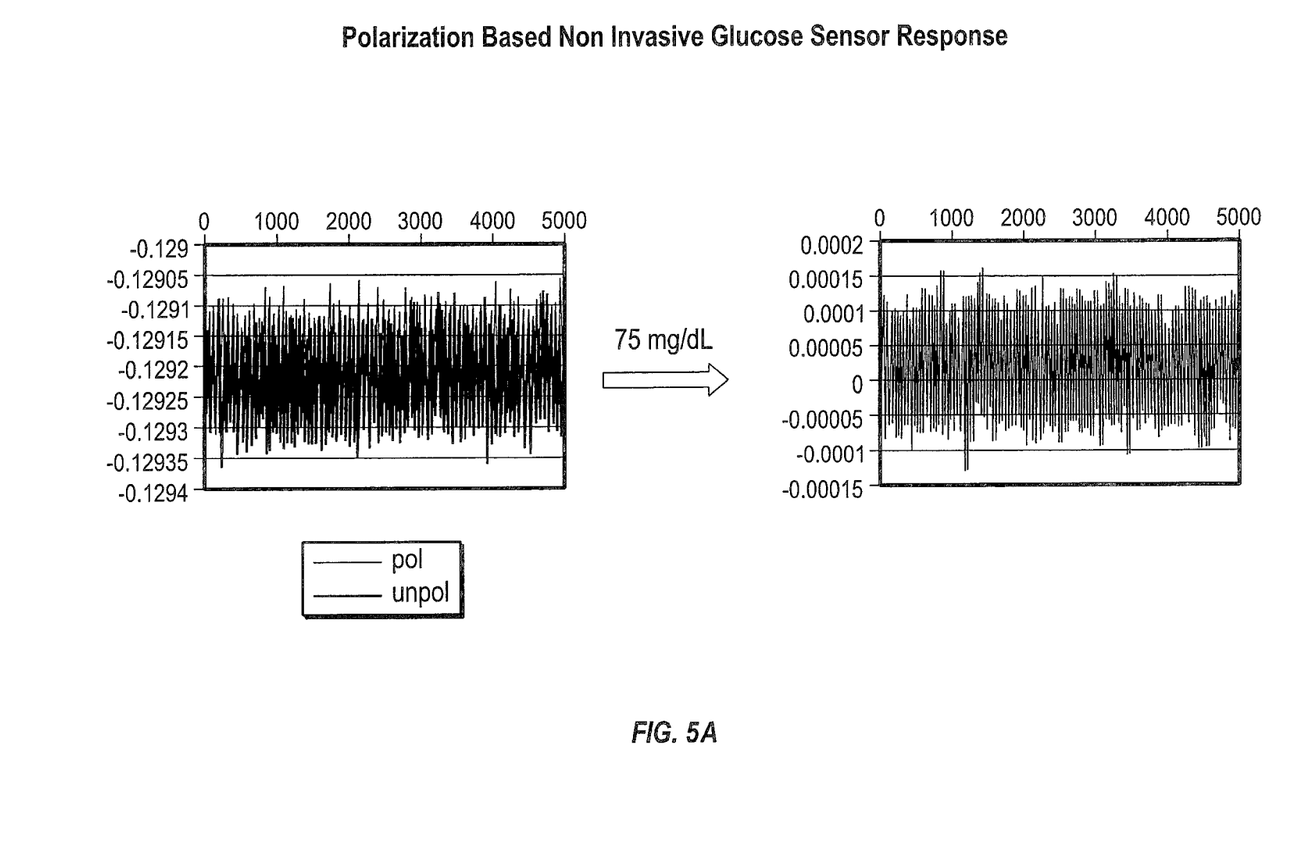
FIG. 5A-5C show the same data shown in FIGS. 4A-4C in a different form, with the unpolarized and polarized waveforms imposed on one another.
Figure 5B:
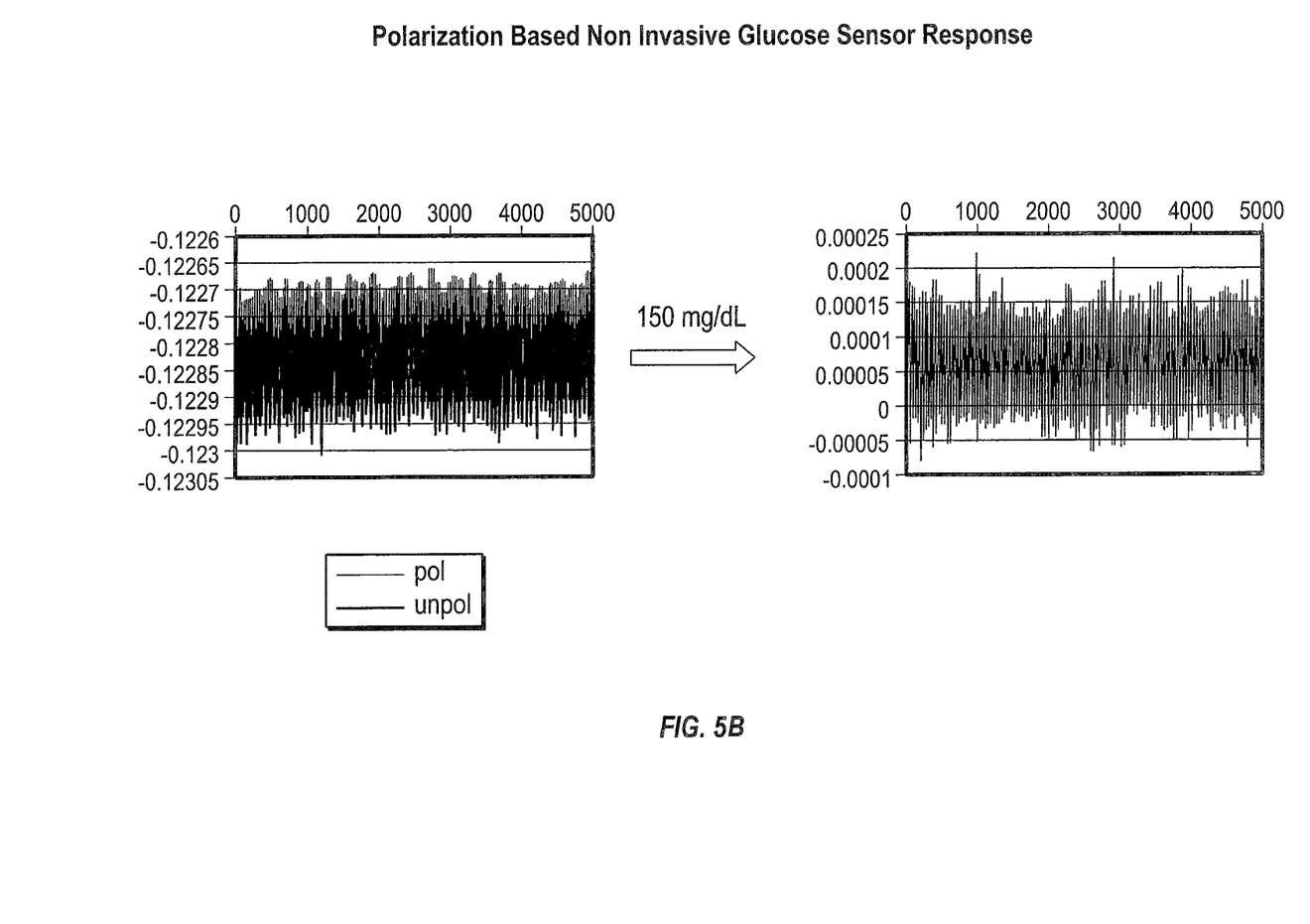
Figure 5C:
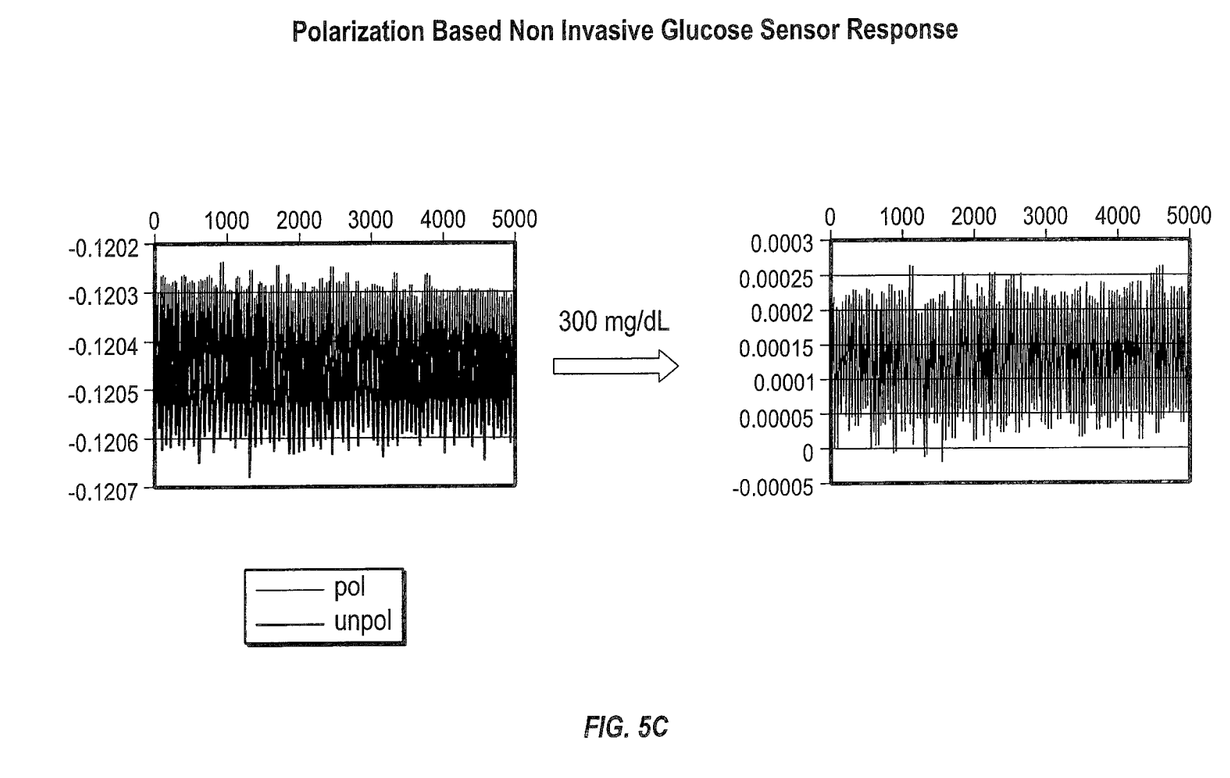

FIGS. 5A-5C show the same data depicted in FIGS. 4A-4C, but with the unpolarized and polarized waveforms on the same graph. FIG. 5A corresponds to the data shown in FIG. 4A. FIG. 5B corresponds to the data shown in FIG. 4B. FIG. 5C corresponds to the data shown in FIG. 4C.

The present disclosure includes preferred or illustrative embodiments in which specific sensors and methods are described. Alternative embodiments of such sensors can be used in carrying out the invention as claimed and such alternative embodiments are limited only by the claims themselves. Other aspects and advantages of the present invention may be obtained from a study of this disclosure and the drawings, along with the appended claims.

I claim:

1. A system for measuring a change in polarization of energy across a fluid, the system comprising:
   a single source for emitting energy;
   a first polarizer for polarizing the energy emitted from the source to provide a first polarized energy;
   a second polarizer for polarizing at least a portion of the first polarized energy and to provide a second polarized energy, wherein the second polarizer is rotated by a rotational amount with respect to the first polarizer;
   a first detector for detecting the first polarized energy received a distance away from the first polarizer;
   a second detector for detecting the second polarized energy; and
   a module coupled with the first detector and the second detector, the module comprising a first unit for receiving output from the first detector and a second unit for receiving output from the second detector, the module comparing the first and second outputs.

2. The system of claim 1, wherein said first unit of the module comprises an attenuator for reducing at least a portion of the output from the first detector.

3. The system of claim 1, wherein said second unit of the module comprises a compensator for boosting at least a portion of the output from the second detector.

4. The system of claim 1, wherein said system comprises a subtractor for reducing at least a portion of the output from the first detector.

5. The system of claim 1, wherein the energy is in the form of light emitted in a near infrared frequency range.

6. The system of claim 1, wherein the polarizer is selected from a film, wire grid, holographic wire grid, and beamsplitter.

7. The system of claim 1, wherein the second polarizer is rotated by a rotational amount that is at least about 45 degrees or a multiple of about 45 degrees.

8. The system of claim 1 further comprising a signal amplifier for amplifying output from the module.

9. The system of claim 1, wherein the apparatus is fitted to an ear such that the first polarizer is on a first facing surface of an ear while the second polarizer, the first detector, the second detector and the module are on an opposing second facing surface of the ear.

10. A system for measuring a change in polarization of energy across a portion of a human body part, the system comprising:
    a first polarizer for polarizing energy emitted from a source and to provide a first polarized energy to a first facing surface of the human body part;
    a second polarizer for polarizing at least a portion of the first polarized energy received from the first polarizer when positioned on a second opposing facing surface of the human body part;
    a first detector for detecting at least a portion of the first polarized energy when received on the second opposing facing surface of the human body part;
    a second detector for detecting at least a portion of the second polarized energy when received on the second opposing facing surface of the human body part; and
    a module operably coupled the first detector and the second detector on the second opposing facing surface of the human body part, the module comprising a first unit for receiving output from the first detector and a second unit for receiving output from the second detector, the module using the outputs from the first and second units to derive a glucose concentration.

11. The system of claim 10, wherein the second polarizer is rotated by a rotational amount with respect to the first polarizer.

12. The system of claim 10, wherein the rotational amount is between and includes 35 degrees and 55 degrees.

13. The system of claim 10, wherein the system further comprises at least a first band pass filter to filter the output from the first detector and a second band pass filter to filter the output from the second detector.

14. An apparatus for measuring change in sugar concentration in a subject fluid, the apparatus comprising:
    a source of energy, the source having an emitter with an emission pattern;
    a first detector spaced a distance from the source;
    a second detector collocated with said first detector;
        a plurality of polarizers between the source and the detectors, the plurality of polarizers comprising at least:
            a first polarizer intersecting the emission pattern; and
            a second polarizer rotated relative to the first polarizer by a first rotational amount θ, spaced a distance from the first polarizer, and proximal to said second detector, wherein the first polarizer is between the source and the second polarizer.

15. The apparatus of claim 14 wherein the distance between the first polarizer and the second polarizer enables the positioning of a volume of liquid intersecting the emission pattern between the first polarizer and the second polarizer and optically between the first polarizer and the first detector.

16. The apparatus of claim 14 further comprising at least one circuit coupled to the first detector and the second detector.

17. The apparatus of claim 16, the at least one circuit comprising:
    a compensating circuit coupled to the second detector;
    a subtractor circuit coupled to the compensating circuit and said first detector; and
    a gain circuit coupled to said subcontractor circuit.

18. The apparatus of claim 17 wherein the compensating circuit comprises a unity gain circuit coupled to and between the second detector and the subtractor circuit.

19. The apparatus of claim 17 wherein the compensating circuit comprises an attenuator coupled to and between first detector and the subtractor circuit.

20. The apparatus of claim 14, wherein the plurality of polarizers consists of the first polarizer and the second polarizer.

21. The apparatus of claim 14, wherein the energy is unmodulated.

22. The apparatus of claim 14, wherein the energy source is a LED.

23. The apparatus of claim 14 wherein $\Theta$ is between thirty-five and fifty-five degrees inclusive of rotation from a baseline rotation caused by a baseline concentration of a simple sugar in a fluid for energy traveling a length L through said fluid.

24. The apparatus of claim 23 wherein $\Theta$ is between forty and fifty degrees inclusive.

25. An apparatus for measuring change in sugar concentration in a fluid relative to a baseline concentration, the apparatus comprising:
- a source of energy, said source having an emitter with an emission pattern;
- a first detector spaced a distance from said source;
- a second detector collocated with said first detector;
- a first polarizer intersecting the emission pattern;
- a second polarizer rotated relative to the first polarizer by a first rotational amount $\Theta$, spaced a distance from the first polarizer, and proximal to said second detector, wherein said first polarizer is optically between said source and said second polarizer;
- a volume of liquid, said volume intersecting said emission pattern and positioned between said first polarizer and said second polarizer and between said first polarizer and said first detector; and
- at least one circuit coupled to said first detector and said second detector, said at least one circuit comprising:
  - a compensating circuit coupled to said second detector;
  - a subtractor circuit coupled to said compensating circuit and said first detector; and
  - a gain circuit coupled to said subtractor circuit.

* * * * *